United States Patent [19]

Hedrick

[11] Patent Number: 4,650,689
[45] Date of Patent: Mar. 17, 1987

[54] PROCESS FOR ETHANOL PRODUCTION FROM CELLULOSIC MATERIALS

[75] Inventor: William S. Hedrick, Golden, Colo.

[73] Assignee: Urban Fuels, Inc., Denver, Colo.

[21] Appl. No.: 715,932

[22] Filed: Mar. 25, 1985

[51] Int. Cl.$^4$ .................. C12C 3/00; F24C 15/10; C12P 7/06
[52] U.S. Cl. ..................................... 426/600; 127/37; 435/161
[58] Field of Search .......................... 127/37; 426/600; 435/161

[56] References Cited

U.S. PATENT DOCUMENTS

| | | | |
|---|---|---|---|
| 1,511,786 | 10/1924 | Terrisse et al. | 127/37 |
| 1,670,727 | 5/1928 | Kocher | 127/37 |
| 1,963,972 | 6/1934 | Dreyfus | 127/37 |
| 4,556,432 | 12/1985 | Erckel | 127/37 |

FOREIGN PATENT DOCUMENTS 107219  6/1917  United Kingdom .................. 127/37

Primary Examiner—Jeanette Hunter
Attorney, Agent, or Firm—Timothy J. Martin

[57] ABSTRACT

A method for producing a fermentable wort useful to produce ethanol from cellulosic materials is particularly adaptable for batch-wise processing. The broad method includes the steps of placing the materials in an airtight vessel that is evacuated to a moderate vacuum at a reduced temperature of 20° C. or less. Highly concentrated mineral acid gas, such as HCl, is introduced to raise the vessel pressure to a pressure less than 1500 mm of Hg wherein the concentration of acid gas is at least 40%. These temperatures and pressures are maintained for at least 30 minutes to depolymerize the cellulose after which the vessel is again evacuated to remove the excess gas and then raised to ambient pressure so that the material is removed. The depolymerized material, which contains some adsorbed acid gas, is mechanically conveyed against a counterflow of hot water. The hot water thus dissolves a portion of the adsorbed gas to produce a weak acid solution of between 2% and 4% which hydrolyzes the depolymerized cellulose to produce the wort. The water flow also produces an enriched zone of dissolved sugars so that the wort is drawn off from the enriched zone after which it may be fermented and distilled into ethanol.

19 Claims, 1 Drawing Figure

PROCESS FOR ETHANOL PRODUCTION FROM CELLULOSIC MATERIALS

BACKGROUND OF THE INVENTION

The present invention concerns the production of ethanol from cellulosic materials and, in particular, the production of a wort from materials containing cellulose, such as scrap paper, wood or paper pulps, and the subsequent fermentation and distillation of this wort into ethanol. The process described may be implemented by both large and small scale systems in order to obtain favorable economic yields, and this process is particularly suitable for batch-wise production of fermentable wort.

The production of basic sugars from cellulosic materials has been known for some time, as has the subsequent fermentation and distillation of these sugars into ethanol. Much of the prior art development occurred around the time of World War II when fuels were a premium in such countries as Germany, Japan and the Soviet Union. These early processes were primarily directed to acid hydrolysis but were fairly complex in their engineering and design and were very sensitive to small variations in process variables, such as temperature, pressure and acid concentrations. A comprehensive discussion of these early processes, as well as some more modern techniques, is thoroughly presented in "Production of Sugars From Wood Using High-pressure Hydrogen Chloride", *Biotechnology and Bioengineering*, Volume XXV, at 2757-2773 (1983).

The abundant supply of petroleum in the period from World War II through the early 1970s slowed ethanol conversion research. However, due to the oil crisis of 1973, researchers increased their efforts in developing processes for the utilization of wood and agricultural byproducts for the production of ethanol as alternate energy sources. This research was especially important for development of ethanol as a gasoline additive to reduce the dependency of the United States upon foreign oil production, to increase the octane rating of fuels, and to reduce exhaust pollutants as an environmental measure.

Concurrently with the "oil crisis," as it became known, the Environmental Protection Agency of the United States promulgated regulations requiring the reduction of lead additives in an effort to reduce air polution. Insofar as ethanol is virtually a replacement of lead, some refineries have selected ethanol as the substitute, especially since it can easily be introduced into a refinery's operation without costly capital equipment investment.

In addition to improving the prior high pressure and high temperature HCL gas saccharification processes developed decades ago, current research is directing its efforts primarily in the enzymic conversion processes such as that employed by the University of Arkansas and that being developed by the Massachusetts Institute of Technology. These processes employ the use of enzymes, such as thermophilic organisms (e.g. clostridium thermocellum) which breaks the cellulose into fermentable sugars. Uncertainty still remains with these processes and their ability to be scaled up for commercialization as well as their relatively slow rates of ethanol production. A continuous acid-hydrolysis process is proposed by researchers at New York University wherein a plug of cellulose substrate is injected with steam to break the cellulase and lignin bond. This system has fairly narrow operating tolerances, high energy input and experiences difficulty in being scaled up for commercialization. An acid/methanol process utilizing hot sulphuric acid at a two percent concentration has been developed as the Purdue University/Tsao process, but the commercial viability of this process is still questioned. These prior art processes, as well as many others, are described in a report entitled "Energy from Biological Processes," Congress of the Unites States, Office of Technology Assessment (July 1980).

One of the largest potential sources for "new materials" containing levels of cellulose suitable for conversion into ethanol is waste paper. Although the demand for waste paper used for both recycling and for waste-to-energy programs is increasing, current projections show that at least for the next 20 years, many tons of material will still be collected and disposed at land fills. This is true even through the conversion of waste paper into ethanol is indisputably more economical than land filling due to the cost of waste disposal, particularly land costs and transportation costs associated with land fill operations. In addition to these costs, there are the problems confronted with environmental regulation as well as the aesthetic degradation where a land fill is employed.

Despite the availability of the techniques mentioned above which techniques produce ethanol from cellulosic materials, there remains a need for a simple method for ethanol conversion which takes advantage of low cost equipment and does not consume massive quantities of processing materials, such as mineral acid. There is further need for such a process that may be implemented in both large and small scale operations in order to avoid the uneconomical costs of transporting cellulosic wastes and which avoids the aesthetic cost of land fill operations.

SUMMARY OF THE INVENTION

It is an object of the present invention to provide a new and useful method for producing a fermentable work from cellulosic materials in a simple yet effective manner.

It is another object of the present invention to provide a method for producing ethanol which method utilizes simple procedures and relatively low cost equipment and which may be employed on both large and small scale operations.

Yet another object of the present invention is to provide a process for producing ethanol from cellulosic materials, such as waste paper, in a manner that does not consume large quantities of processing materials.

It is still a further object of the present invention to provide a method for converting waste paper to fermentable sugars using a two stage mineral acid treatment process whereby most of the acid is recoverable for reuse.

It is still a further object of the present invention to provide a method for producing ethanol from cellulosic materials which method is tolerant to variations in process parameters over manageable ranges.

The present invention is directed to accomplishing these objects by providing a method for producing ethanol from material containing cellulose, such as waste paper and the like. Naturally, this method may be employed with any material containing suitable levels of cellulose so that the economic "break-even" of the process is exceeded.

The method of this invention broadly contemplates a batch-type process wherein cellulosic materials are placed in a substantially air-tight vessel that is evacuated to a moderate vacuum with the materials being cooled to a reduced temperature no more than approximately 20° C. After the evacuation, highly concentrated mineral gas, such as hydrogen chloride, is introduced into the vessel while the material therein is maintained at the reduced temperature. Preferably, the mineral acid gas is precooled before introduction into the vessel since both the adsorption of the gas and the chemical reaction between the cellulose and the gas tends to warm the material. The pressure at this first processing state is maintained between 400 and 1500 mm of Hg, inclusive; and the material is held at the first processing stage for more than 30 minutes during which a portion of the cellulose is depolymerized while a portion of the mineral acid gas is adsorbed.

After the first processing stage, the vessel is evacuated to a pressure less than 400 mm of mercury to remove most of the mineral acid gas that is in the gaseous state while allowing the adsorbed gas to remain with the depolymerized cellulosic material. The pressure of the vessel is then raised to the ambient pressure and the material is removed. The depolymerized material is then hydrolyzed by bathing the material in a hot water bath where the water temperature is approximately 100° to 120° C. The adsorbed mineral acid gas is dissolved in sufficient hot water to produce a relatively weak acid solution of two to four percent that then hydrolyzes depolymerized cellulose to form a wort. This wort may then be fermented into an ethanol solution that is then distilled into a useable ethanol product.

Preferably, the hot water bath is conducted as a counterflow wherein the depolymerized cellulose is mechanically conveyed against the a counterflow of hot water. An initial portion of hot water thus forms an enrichment zone of increased concentration of sugars when the depolymerized cellulose is hydrolyzed. The wort of this enriched zone, having an increased concentration of sugar, is then removed for subsequent fermentation and distillation. In addition, the residue material, formed after the wort is removed, may be used either as a feed, for example as cattle feed, or as a fertilizer. To this end, it is sometimes desirable to neutralize the residue material by adding an alkaline material thereto. This may conveniently be accomplished by the addition of anhydrous ammonia to the residue so that its pH is neutralized and nitrogen is introduced into the residue. This enhances the value of the residue for both feeding and for fertilizer use.

These and other objects of the present invention will become more readily appreciated and understood from a consideration of the following detailed description of the preferred embodiment when taken together with the accompanying drawings, in which:

DETAILED DESCRIPTION OF THE PREFERRED EMBODIMENT

Figure 1:
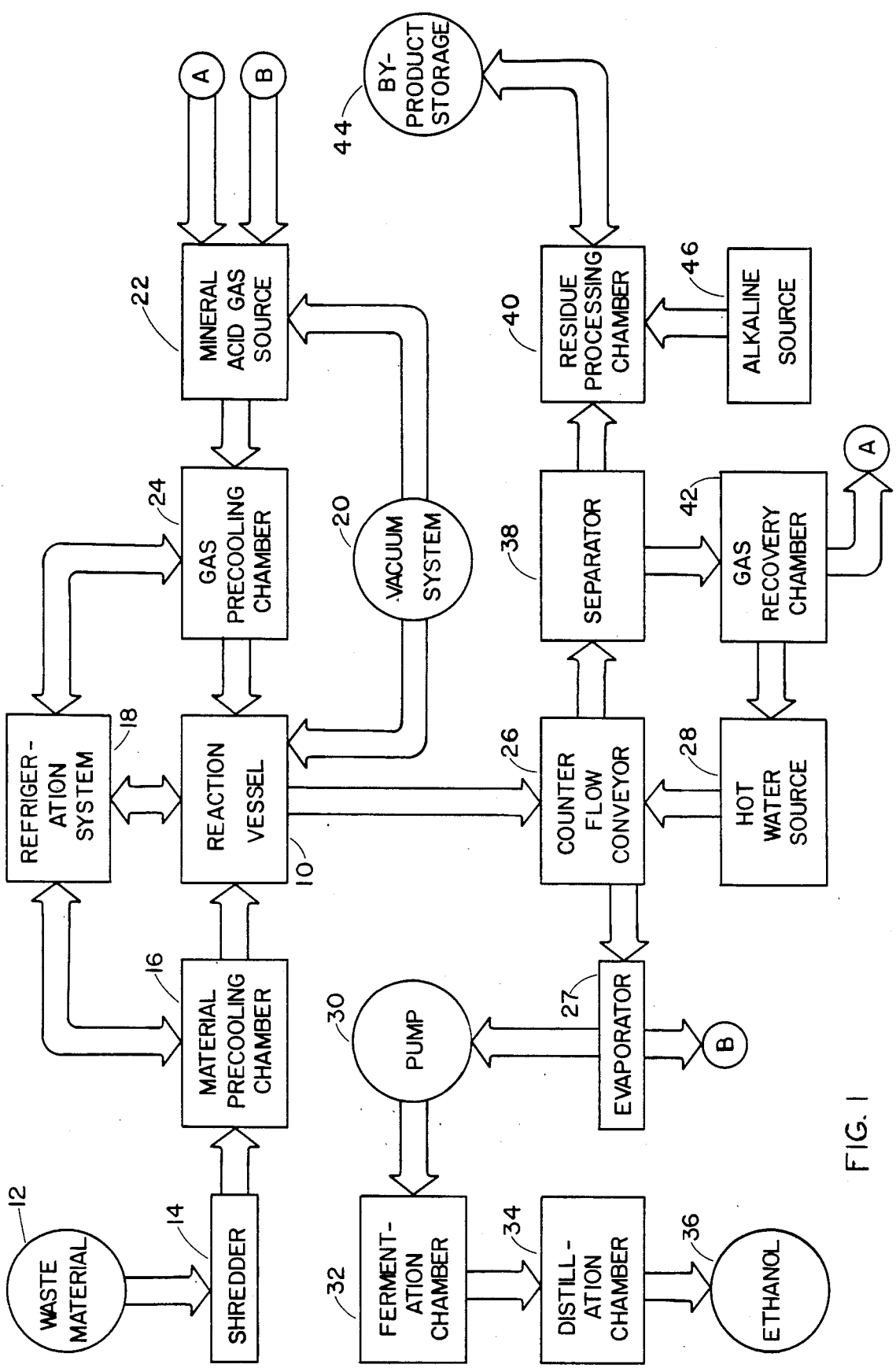
FIG. 1 is a block diagram of a system used to accomplish the method according to the preferred embodiment of the invention described herein.

The present invention is directed to a process for producing a fermentable wort from materials containing cellulose, and in particular, is useful for processing waste paper or cellulose fines, the latter being a by-product of paper manufacturing mills. Specifically, the present invention is designed to be a batch process so that it may be used for both large scale and small scale operations. Since it may be used for small scale operations, localized conversion of waste products into ethanol becomes possible thereby eliminating the high costs of transporting the raw materials for treatment. At the same time, the present invention's applicability to large scale systems permits the process to be utilized to process large volumes of waste materials at locations where large volumes of the cellulosic materials are produced.

As may be seen in FIG. 1, cellulosic material is placed in a reaction vessel 10 for an initial processing stage. Typically, waste paper may be stored in a storage bin 12 after which it is passed through a shredder 14 so that it is reduced to a desired particulate size and consistency prior to its introduction into reaction vessel 10. The step of shredding a paper product is helpful to prevent unwanted matting of the material during the first processing stage, described below. The first processing stage is conducted in vessel 10 at a reduced temperature at or below 20° C. and preferably within the range of 0° C. to 20° C. This helps avoid the production of unwanted degradation by-products that occur with higher temperature prior art processes.

In order to insure that the raw material in the form of waste paper is initially within this temperature range, the material is passed from shredder 14 into a precooling chamber 16 that is cooled by refrigeration system 18. The cooled waste material is then placed in reaction vessel 10 which is in the form of a substantially air-tight vessel that may maintain a moderate vacuum. It is completely within the scope of this invention, however, that the cooling of the raw material for processing occur in reaction vessel 10. Precooling chamber 16 thus may be a suitably sized refrigeration chamber that physically receives vessel 10.

Once the material for processing is placed in reaction vessel 10 and the desired temperature range of 0° C. to 20° C. obtained, the vessel is evacuated to a moderate vacuum of approximately 70 to 100 mm of Hg by vacuum system 20. A highly concentrated mineral gas, such as HCL, from mineral gas source 22 is then introduced into reaction vessel 10 through a gas precooler 24 which reduces the temperature of the mineral gas to within the desired temperature range. Gas precooler 24 may be driven by coolant from refrigeration system 18 which was previously described.

Reaction vessel 10 is pressurized with the mineral gas to a pressure that does not exceed 1500 mm of Hg, and is preferably in a range of 400 to 1500 mm of Hg, inclusive, so that the first processing stage may be conducted. The mineral acid gas is preferably hydrogen chloride, although it is within the scope of this system to use other mineral acid gases such as sulfur dioxide, sulfur trioxide, or any other highly concentrated mineral acid gas that would react with the cellulose in the waste material to depolymerize the cellulose into basic sugars. This first processing stage is then maintained for a period of time in excess of 30 minutes, and preferably for a time interval of 30 minutes to 120 minutes to allow depolymerization of the cellulosic material. During this first stage, the temperature of the cellulosic material is held in the desired reduced first temperature range so that degradation of the cellulose does not take place. It is important that degradation be avoided since the degradation by-products can inhibit the fermentation step necessary to convert the sugars produced by this process into ethanol. The pressurization of vessel 10 is selected so that the concentration of acid gas is at least 40%.

After the time period set for the first stage, the vacuum system is again operated to remove the mineral acid gas from reaction vessel 10 until the presure of reaction vessel 10 is reduced to a pressure less than 400 mm of mercury. During this evacuation, the recovered mineral acid gas may be conveyed by vacuum system 20 back to mineral acid gas source 22 for reuse.

It should also be noted that, due to physical and chemical properties of the cellulosic material, a certain portion of the mineral acid gas, under the pressures described, become adsorbed by the material and this adsorption is an important element of this process. Once the mineral acid gas is removed from reaction vessel 10, air is inletted into reaction vessel 10 to raise the internal pressure to the ambient pressure so that reaction vessel 10 may be opened to remove initially processed material therefrom. This initially processed material now contains significant quantities of deploymerized cellulose that is ready for hydrolysis into basic sugars.

In order to hydrolyze the first processed material, the material is preferably placed on a mechanical conveyer 26 and is moved in a first direction against a flow of water from a hot water source 28. A convenient commercially available counterflow conveyor is an auger conveyor manufactured by Beloit Corporation of Dalton, Mass. As the material moves through the counterflow of hot water, two things happen. First, a large portion of the previously adsorbed mineral acid gas becomes dissolved in the hot water to form a weak acidic solution. Hence, it is important that the water volume flow and evacuation pressures be selected so that the adsorbed mineral acid gas goes into solution at concentration levels to form an acidic solution of between two to four percent. This weak acid solution then hydrolyzes the depolymerized cellulose into dissolved basic sugars. Second, as the water flow and the subsequent weak acid solution flows through the first processed material, an initial portion of the water increases in concentration of sugars so that it forms an enrichment zone of dissolved sugars in the water solution thereby defining a wort from which ethanol may be produced. The amount of water that is passed through the processed material is selectively adjusted so that the wort derived preferably contains a concentration of sugar within a range of 15% to 25% by weight.

A pump 30 is provided to remove wort from counter flow conveyer 26 at the enrichment zone and convey the wort into a fermentation chamber 32 thereby leaving second processed material in conveyer 26. After suitable fermentation, as is known in the art, the fermented wort is distilled by a distillation system 34 to produce recoverable liquid ethanol at numeral 36. The fermentation and distillation of this wort is generally known in the art, and forms part of this invention only when used in conjunction with the production of the wort described above. Prior to the introduction of the wort into fermentation chamber 32, the wort may be passed through an evaporator 27 in order to remove any excess mineral acid gas which may be returned to gas source 32, as at B, or which may otherwise be disposed.

After the wort is removed from counter flow conveyer 26, the second processed material is removed therefrom and placed in a separator 38. Separator 38 may be a standard centrifuge, such as manufactured by Sharples-Stokes Corporation of Warminster, Pa., or a separating screen, such as manufactured by Sweco, Inc., of Los Angeles, Ca.. Separator 38 is employed to separate the second processed material into a relatively solid byproduct that is placed in residue processing chamber 40 and a liquid by-product that is placed in gas recovery chamber 42. Gas recovery chamber 42 removes the mineral acid gas from the liquid by-product at A and returns the recovered acid gas back to mineral acid gas source 22 for reuse. The remaining hot water from gas recovery chamber 42 may then be returned to hot water source 28 for reuse by counter flow conveyer 26. In the alternative, the hot water from gas recovery chamber 42 may be passed through the heat exchanger so that heat is recovered and used to heat hot water at source 28 rather than being mixed therein.

As noted, the solid residue from separator 38 is placed in processing chamber 40 where it may be neutralized by adding an alkaline neutralizing material from alkaline source 46. Typically, such neutralizing material may be anhydrous ammonia, and should be added in sufficient quantities so that the acidic pH of the residue in processing chamber 40 is raised to a neutral level and to add nitrogen to the residue. The neutralized by-product may then be stored in by-product storage 44 for use either as fertilizer or as an animal feed source.

As noted above, rather than being a continuous process, the method described with respect to the preferred embodiment contemplates a batch method of producing ethanol, and, as such, is much different from the continuous processes described in the prior art known by the applicant. In this batch process, it is preferable that a plurality of reaction vessels 10 be employed and be in the form of large cylinders approximately 0.5 to 1.5 meters in diameter with lengths of from three to 10 meters. The cylinders should have openable closures at each end so that a piston-like ram mechanism may be used to load and unload the cellulosic material, such as shredded waste paper, which is processed in a cylinder. After loading, the entire cylinder is placed in the pre-cooling chamber so that the contents are reduced in temperature to within the desired reduced temperature range. After a first cylinder is removed from the pre-cooling chamber, it is evacuated by vacuum system 20 and precooled hydrochloric gas is introduced therein and the first processing stage is carried out. During this time, another similar reaction vessel is cooled by refrigeration system 18 and evacuated, so that, when vacuum system 20 removes the acid gas from a first reaction vessel 10 after the first processing stage, the gas may be introduced into the second reaction vessel so that the gas is reused by each subsequent reaction vessel and additional gas is added from mineral acid gas source 22, only as required.

Thus, the present invention further contemplates a batch process where a plurality of batches, each in a separate reaction vessel, are sequentially processed by this method. Accordingly, fermentation chamber 32 may receive wort from counter flow conveyer 26 which wort comprises liquid material from several batches so that fermentation and distillation may be on a larger scale, if desired.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present inven-

What I claim is:

1. A method for producing a fermentable wort from material containing cellulose, comprising the steps of:
   placing said materials in a substantially air-tight vessel and evacuating said vessel to a vacuum of less than or equal to 100 mm Hg with said material being at a temperature within a base temperature range equal to or less than 20° C.;
   introducing a concentrated mineral acid gas into said vesel while maintaining the temperature of said material within said base temperature range and at a pressure less 1500 mm Hg to define a first processing stage wherein the concentration of said mineral acid gas is at least 40%;
   holding said material at the first processing stage for more than thirty minutes whereby a portion of the cellulose is depolymerized and a portion of said mineral acid gas is adsorbed by said materials;
   evacuating said vessel to a pressure less than 400 mm of mercury to remove some of said mineral acid gas;
   raising the pressure of said vessel to the ambient pressure after which the material is removed therefrom;
   conveying said material in a first direction along a conveyor apparatus and counterflowing hot water in a second direction against the flow of material whereby the adsorbed mineral acid gas is dissolved to produce a weak acid solution at a sufficient level to hydrolyze the depolymerized cellulose and whereby a first portion of the hot water makes intial contact with the material to define an enrichment zone that becomes increasingly more concentrated with sugars from the depolymerized and hydrolyzed cellulose; and
   removing hot water and sugars as a wort from the enrichment zone.

2. The method according to claim 1 wherein said mineral gas is selected from a group consisting of hydrogen chloride gas, sulfur dioxide gas and sulfur trioxide gas.

3. The method according to claim 2 wherein said material is separated into a solid residue and said wort after the material is bathed in the hot water bath and including the step of adding a sufficient amount of alkaline material to said residue to substantially neutralize the acidity thereof.

4. The method according to claim 3 including the step of evaporating dissolved mineral acid gas from said wort.

5. The method according to claim 3 including the step of adding nitrogen to the residue.

6. The method according to claim 5 wherein said alkaline material is anhydrous ammonia.

7. The method according to claim 1 wherein said material is cooled during the evacuation of said vessel to a temperature within said base temperature range.

8. The method according to claim 7 wherein the mineral acid gas is pre-cooled to a temperature within the base temperature range prior to its introduction into said vessel.

9. The method according to claim 1 wherein said base temperature range is between 0° and 20° C.

10. The method according to claim 1 wherein the amount of hot water and the pressure for evacuating the mineral acid gas are selectively adjusted so that the adsorbed mineral acid gas goes into solution at concentration levels to form an acidic solution of between two to four percent, inclusive.

11. The method according to claim 10 wherein the amount of hot water is sufficient so that the wort in the enrichment zone contains a concentration of sugars within a range of 15% to 25%, inclusive, by weight.

12. The method according to claim 1 wherein said first processing state is held for a time between thirty and one hundred twenty minutes.

13. The method according to claim 1 wherein the step of raising the vessel to ambient pressure is accomplished by inletting air into the vessel.

14. The method according to claim 1 wherein said wort is fermented into an ethanol solution and said ethanol solution is distilled.

15. A method for producing a fermentable wort from a polymerized cellulosic material, comprising the steps:
   placing the cellulosic material in a substantially air-tight vessel and evacuating the vessel to a first pressure state of less than or equal to 100 mm of Hg with said material at a first temperature between a base temperature range of 0° to 20° C.;
   introducing a concentrated mineral acid gas having a temperature within said base temperature range whereby the mineral acid gas pressurizes the vessel to a second pressure state of between 400 mm Hg and 1500 mm Hg to define a first processing stage;
   holding said first processing stage for at least thirty minutes while maintaining the temperature within the vessel within the first temperature range whereby a portion of the polymerized cellulosic material is depolymerized and a portion of said acid gas is absorbed by the cellulosic material to form a processed material;
   evacuating said vessel to a pressure less than 400 mm Hg to remove some of said acid gas;
   pressuring the vessel to ambient pressures and removing processed material from the vessel;
   mechanical conveying said processed material against a counterflowing stream of hot water whereby at least some of the adsorbed mineral gas is dissolved into the water to produce a weak acid at a sufficient level to hydrolize the depolymerized cellulose into sugars and whereby a downstream portion of the hot water stream defines an enrichment zone comprising a wort having an increased concentration of sugars; and
   removing the wort from said enrichment zone.

16. The method according to claim 15 wherein ethanol is produced by fermenting and distilling said wort.

17. A batch process for producing a fermentable wort from polymerized cellulosic materials, wherein each successive batch process comprising the steps of:
   placing the cellulosic materials in a substantially air-tight vessel and evacuating said vessel to a moderate vacuum within a first pressure range of less than or equal to 100 mm of Hg with said materials having a first temperature within a base temperature range of less than or equal to 20° C.;
   introducing a concentrated mineral acid gas having a gas temperature within said base temperature range in an initial amount sufficient to pressurize the first vessel to a first process pressure within a process pressure range of 400 and 1500 mm Hg, inclusive, while maintaining the temperature in the first vessel within the base temperature range to define a first process stage;

holding said first process stage for at least thirty minutes whereby a portion of the polymerized cellulosic material in said first vessel is depolymerized and a portion of said initial amount of the acid gas is adsorbed by the cellulosic material to form a processed material;

evacuating said first vessel to an intermediate pressure at or less than 400 mm Hg to remove and exhaust the acid gas after which the vessel is pressurized to the ambient pressure and the processed material is removed, the acid gas used in said step of introducing concentrated mineral acid gas including exhaust acid gas from previous batch processes;

mechanically conveying processed material against a counterflowing stream of hot water whereby at least some of the adsorbed acid gas is dissolved into the water to produce a weak acid at a sufficient strength to hydrolyze the depolymerized cellulose into sugars and to produce an enriched zone of said sugars as the stream of water moves through the conveyed processed materials; and removing the wort from said enriched zone.

18. The method according to claim 17 including the step of recovering acid gas from water after said wort is removed and combining the recovered acid gas with the exhaust gas for use in successive batch processes in the first processing stack.

19. A method for producing a fermentable wort from material containing cellulose, comprising the steps of:

placing said materials in a substantially air-tight vessel and evacuating said vessel to a vacuum of less than 100 mm of Hg with said material being at a temperature within a base temperature range equal to or less than 20° C.;

introducing a mineral acid gas into said vessel while maintaining the temperature of said material within said base temperature range and at a pressure less 1500 mm Hg to define a first processing stage wherein the concentration of said mineral acid gas is at least 40%;

holding said material at the first processing stage for a period of time between thirty minutes and two hours whereby a portion of the cellulose is depolymerized and a portion of said mineral acid gas is adsorbed by said materials;

evacuating said vessel to a pressure less than 400 mm of mercury to remove some of said mineral acid gas;

raising the pressure of said vessel to the ambient pressure after which the material is removed therefrom; and bathing said material in a hot water bath of a selected volume of water whereby the adsorbed mineral acid gas is dissolved to produce a weak acid solution at a sufficient level to hydrolyze the depolymerized cellulose whereby said water and said hydrolyed cellulose produces a wort.

* * * * *